United States Patent [19]

Hesse

[11] Plant 5,230

[45] May 8, 1984

[54] CHRYSANTHEMUM PLANT NAMED YELLOW LIMELIGHT

[75] Inventor: Peter S. Hesse, Bradenton, Fla.

[73] Assignee: Pan American Plant Company, Parrish, Fla.

[21] Appl. No.: 407,102

[22] Filed: Aug. 11, 1982

[51] Int. Cl.[3] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Koch

[57] ABSTRACT

A new and distinct cultivar of chrysanthemum plant named Yellow Limelight, and particularly characterized by its flat capitulum form, daisy capitulum type, bright yellow ray floret color, diameter of 35–40 mm. across the face of the capitulum, medium pot plant height, and semi-upright branching pattern.

2 Drawing Figures

The present invention comprises a new and distinct cultivar of *Chrysanthemum morifolium,* Ramat., hereinafter referred to by the cultivar name Yellow Limelight.

Yellow Limelight is a product of a planned mutational breeding program which had the objective of obtaining a cultivar adapted for pot mum culture having a bright clear yellow flower color, as opposed to the white color of the parent cultivar Limelight, a plant patent application for which is pending. The desired characteristics of single daisy capitulum type, nine (9) week flowering response, and year round acceptable commercial quality of the parent cultivar Limelight were desired to be carried over in the mutation. In the controlled mutational breeding program, cuttings or pedicels of the parent cultivar were irradiated in West Chicago, Ill. in 1979 at X-ray radiation levels commonly known and used in the industry.

Yellow Limelight was discovered and selected as one flowering plant within a crop of radiated parent plants by Peter S. Hesse in June, 1979 in a controlled environment in West Chicago, Ill., and given code number 79-YEL. P6-113K-YSD. The first act of asexual reproduction of Yellow Limelight was accomplished when vegetative cuttings were taken from the initial selection on September 1979 in a controlled environment in West Chicago, Ill. by a technician working under formulations established and supervised by Peter S. Hesse. Horticultural examination of selected units initiated in April, 1980 has demonstrated that the combination of characteristics as herein disclosed for Yellow Limelight are firmly fixed and are retained through successive generations of asexual reproduction.

Yellow Limelight has not been observed under all possible environmental conditions. The phenotype may vary significantly with variations in environment such as temperature, light intensity, and day length. The following observations, measurements and comparisons describe plants grown in West Chicago, Ill. and Parrish, Fla. under greenhouse conditions which approximate those generally used in commercial practice.

The following traits have been repeatedly observed and are determined to be basic characteristics of Yellow Limelight, which in combination distinguish this chrysanthemum as a new and distinct cultivar:

1. Flat capitulum form.
2. Daisy capitulum type.
3. Bright yellow ray floret color.

4. Diameter across the face of the capitulum 35–40 mm.
5. Medium pot plant height, approximately 300 mm. from top edge of the pot.
6. Semi-upright branching pattern.

Of the many commercial cultivars known to the present inventor, the most similar in comparison to Yellow Limelight is Yellow Garland, disclosed in U.S. Plant Pat. No. 3,671, dated Dec. 24, 1974. In comparison to Yellow Garland, Yellow Limelight is less sensitive to low temperatures and low light. Under these conditions, Yellow Limelight responds more evenly and is more floriferous than Yellow Garland. The ray floret color, capitulum form and capitulum type are similar to those same characteristics of Yellow Garland. The similarities and dissimilarities between Yellow Limelight and the parent cultivar Limelight are noted above.

The accompanying photographic drawings show typical inflorescence and foliage characteristics of Yellow Limelight, with colors being as nearly true as possible with illustrations of this type. Sheet 1 is color photograph in perspective of Yellow Limelight. Sheet 2 is a black and white photoprint of the underside of typical leaves of various size or location on the plant.

In the following description color references are made to The Royal Horticultural Society Color Chart. The color values were determined between 3:30–4:00 P.M. on May 24, 1982 under 3200K–500W intensity incandescent light at Bradenton, Fla.

CLASSIFICATION

Botanical: *Chrysanthemum morifolium,* Ramat., cv Yellow Limelight.

Commercial: Daisy Pot Mum.

INFLORESCENCE

A. Capitulum:
- *Form.*—Flat.
- *Type.*—Daisy.
- *Diameter across face.*—35–45 mm.

B. Corolla of ray florets:
- *Color (general tonality from a distance of three meters).*—Bright Yellow.
- *Color (abaxial).*—6D.
- *Color (adaxial).*—6A-6B.

C. Corolla of disc florets:
- *Color (mature).*—Yellow.

*Color (immature).*—Lime green.

D. Reproductive organs:

*Androecium.*—Present disc florets only; numerous.

*Gynoecium.*—Present both ray florets and disc florets; numerous.

PLANT

A. General appearance:

*Height.*—Semi-upright, medium plant height, approximately 300 mm from the top edge of pot.

B. Foliage:

*Color (abaxial).*—147B.

*Color (adaxial).*—147A.

*Shape.*—Deeply lobed and slightly serrated.

I claim:

1. A new and distinct cultivar of chrysanthemum plant named Yellow Limelight, as described and illustrated, and particularly characterized by its flat capitulum form, daisy capitulum type, bright yellow ray floret color, diameter of 35–40 mm. across the face of the capitulum, medium pot plant height, and semi-upright branching pattern.

* * * * *

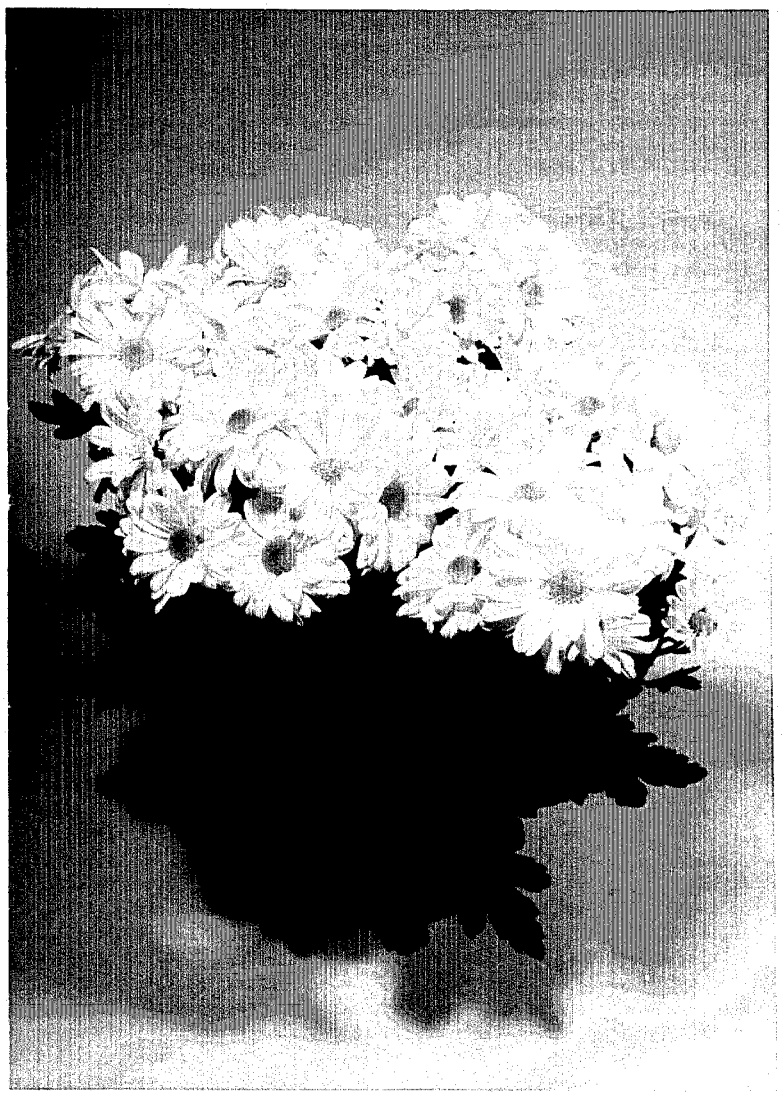

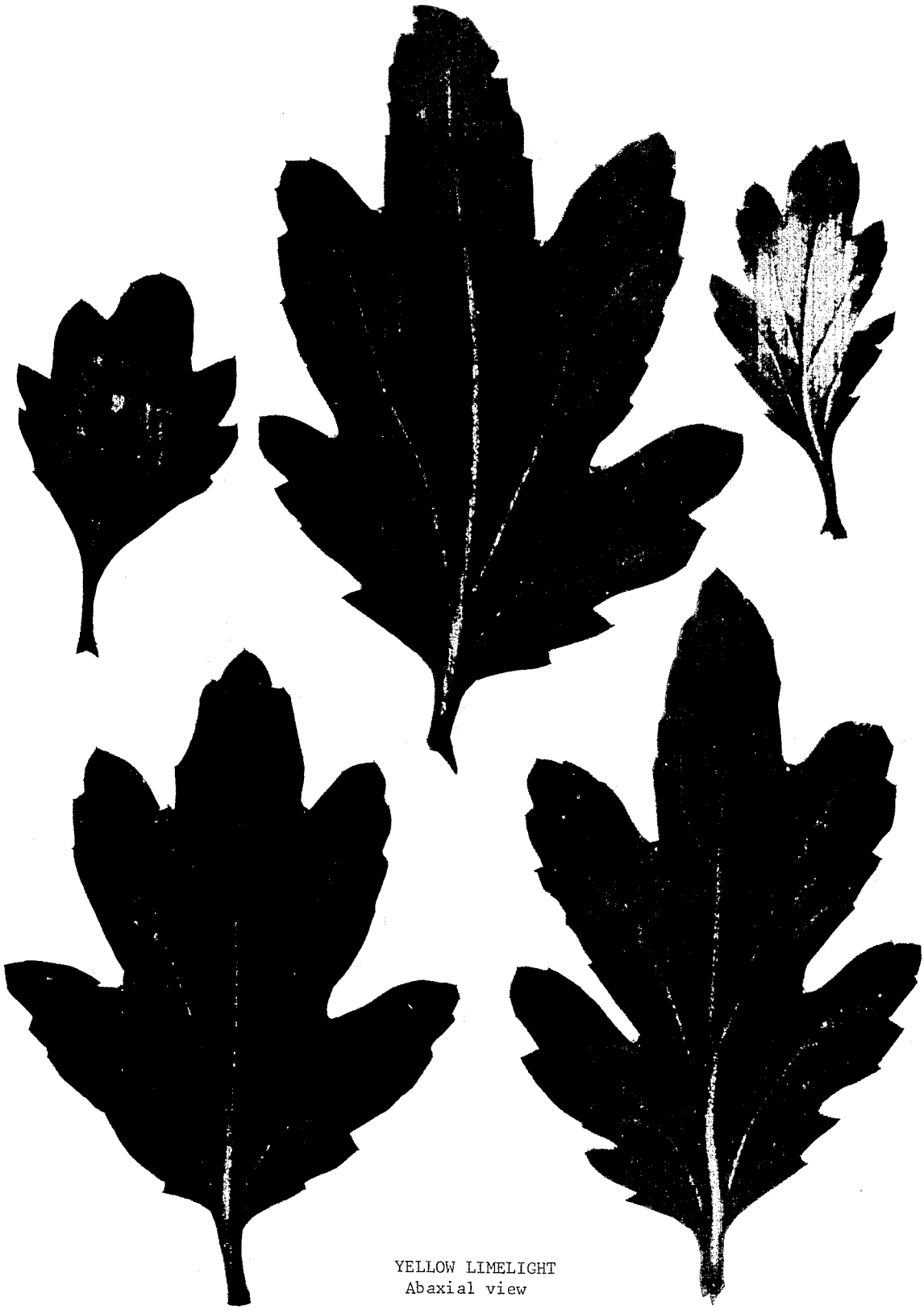
YELLOW LIMELIGHT
Abaxial view